United States Patent [19]
Takayama et al.

[11] Patent Number: 5,158,939
[45] Date of Patent: Oct. 27, 1992

[54] METHOD OF STIMULATING THE IMMUNE SYSTEMS OF ANIMALS AND COMPOSITIONS USEFUL THEREFOR

[75] Inventors: Kuni K. Takayama; Nilofer Qureshi, both of Madison, Wis.

[73] Assignee: Wisconsin Alumni Research Foundation, Madison, Wis.

[21] Appl. No.: 522,446

[22] Filed: May 11, 1990

Related U.S. Application Data

[63] Continuation-in-part of Ser. No. 383,832, Jul. 21, 1989, abandoned, and a continuation-in-part of Ser. No. 467,449, Jan. 19, 1990, Pat. No. 5,041,427.

[51] Int. Cl.$^5$ .................. A61K 31/715; A61K 31/70; A61K 39/00; C12N 1/00
[52] U.S. Cl. ......................................... 514/53; 514/62; 514/885; 536/117; 536/18.7; 536/17.9; 435/822
[58] Field of Search ...................... 514/53, 62, 25, 885; 424/88, 92; 435/72, 74, 84, 85, 100, 131, 822; 536/121

[56] References Cited

U.S. PATENT DOCUMENTS 4,746,742  5/1988  Hasegawa et al. .................. 536/53

OTHER PUBLICATIONS

Strittmatter et al., "Nontoxi Lipopolysaccharide from Rhodopseudomonas sphaeroides ATC 17023," Journal of Bacteriology, Jul. 1983, pp. 153–158.

Cotter et al., "Structural Determination of Lipid A From Gram Negative Bacteria Using Laser Desorption Mass Spectrometry," Biomedical and Environmental Mass Spectormetry, vol. 14, pp. 591–598 (1987).

Takayama et al., "Diphosphoryl Lipid A from *Rhodopseudomonas sphaeroides* ATCC 17023 Blocks Induction of Cachectin in Macrophages by Lipopolysaccharide", Infection and Immunity, Apr. 1989, pp. 1336–1338.

Qureshi et al., 1988, *The Journal of Biological Chemistry*, "Location of Fatty Acids in Lipid A Obtained from Lipopolysaccharide of *Rhodopseudomonas sphaeroides* ATCC 17023," pp. 5502–5504.

Krauss et al. 1989, *Eur. J. Biochem*. 180, 519–526, "Structural Analysis of the nontoxic lipid A of Rhodobacter capsulatus 37b4".

Primary Examiner—Johnnie R. Brown
Assistant Examiner—Everett White
Attorney, Agent, or Firm—Quarles & Brady

[57] ABSTRACT

A method is disclosed for stimulating the immune systems of animals with non-toxic lipid A derivatives. The derivatives include the lipopolysaccharide (LPS) and diphosphoryl lipid A (DPLA) for Rhodopsuedomonas.

6 Claims, No Drawings

METHOD OF STIMULATING THE IMMUNE SYSTEMS OF ANIMALS AND COMPOSITIONS USEFUL THEREFOR

This invention was made with United States Government support awarded by the National Institute of Health (NIH), Grant Nos.: GM-36954, AI-25856. The United States Government has certain rights in this invention.

RELATED CASES

This application is a continuation-in-part of U.S. patent application Ser. No. 07/383,832, filed Jul. 21, 1989, now abandoned, and U.S. patent application Ser. No. 07/467,449, filed Jan. 19, 1990, now U.S. Pat. No. 5,041,427.

TECHNICAL FIELD

This invention relates to in a method of stimulating the immune systems of animals and to novel compositions for use in the method.

BACKGROUND ART

Lipopolysaccharide is a major constituent of the outer membranes of Gram negative bacteria. Studies have shown that it has the following three structural regions: 1) the 0-specific polysaccharide; 2) the common core region; and 3) a lipid component called lipid A. LPS is known to trigger many pathophysiological events in mammals, either when it is injected or when it accumulates due to Gram-negative infection. The lipopolysaccharide (LPS) from *Escherichia coli* is known to stimulate the immune system of animals, but it is relatively toxic.

In general, the hydrophobic lipid A moiety of the LPS is believed to be responsible for the pathophysiological effects of LPS, which also include B-lymphocyte mitogenesis, macrophage activation, interferon production, tumor regression, peripheral vascular collapse ("endotoxic" shock), pulmonary hypertension, pulmonary edema, disseminated intravascular coagulopathy and pyrogenicity.

It is also known that a monosaccharide precursor lipid X has some activity in stimulating 70Z/3 cells and that a large excess of lipid X will compete with lipid A, partially blocking its toxic effects[13]. It is also known that monophosphoryl lipid A from *E. coli* has numerous biological activities associated with LPS, but its toxicity is attenuated[25]. On the other hand, diacyldiphosphoryl lipid A from *E. coli* is known to have very low or no biological activities associated with LPS and it has moderate antagonistic activity against the activation of 70Z/3 cells by LPS (Kirkland and Takayama, unpublished data). It also is known that diphosphoryl lipid A from *E. coli* and Salmonella strains are highly toxic[25].

The LPS obtained from *Rhodopsuedomonas sphaeroides* ATCC 17023 grown at 30° C. was reported to be non-toxic by Strittmatter et. al.[21]. The complete structure of the LPS from this source has now been established[14,18,19]. The structure of the lipid A moiety of the LPS from *R. sphaeroides* is strikingly similar to the lipid A of the toxic enterobacterial and Salmonella LPS[9,22]. The four major differences noted are the presence of a 3-ketotetradecanoate instead of a 3-hydroxytetradecanoate at the 2-position (R4), a Δ[7]-tetradecanoate instead of a tetradecanoate in acyloxyacyl linkage at the 2'-position (R2), the presence of five fatty acids instead of six, and the presence of 3-hydroxydecanoate at the 3-position (R3) instead of 3-hydroxytetradecanoate of the glucosamine disaccharide of the *R. sphaeroides* lipid A. See Formula II for the diphosphoryl lipid A (DPLA) from *R. sphaeroides*.

Another nontoxic LPS from *Rhodopsuedomonas capsulata* ATCC 23782 was reported by Omar et al[27]. The lipid A from the LPS of this source has been prepared and its complete structure determined. This lipid A has 3-ketotetradecanoate at both 2- and 2'-positions (R2 and R4) of the glucosamine disaccharide, a.3-hydroxytetradecanoate at the 3'-position (R3), and Δ[9]-dodecanoyloxydecanoate at the 3'-position (R1) (See Formula III for the structure of the DPLA from *R. capsulata*.)

There is a need for a safe and effective method of stimulating the immune systems of animals.

BRIEF SUMMARY OF THE INVENTION

It is the primary object of the present invention to disclose an effective method of stimulating the immune systems of animals using compositions which are relatively non-toxic.

The method of the present invention comprises stimulating the activity of the immune system of an animal by administering to said animal a safe and effective amount of a non-toxic composition having immunostimulatory activity.

The compositions which are useful in the method of the present invention contain a member selected from a non-toxic LPS from a species of Rhodopsuedomonas or a compound having the following formula:

FORMULA I

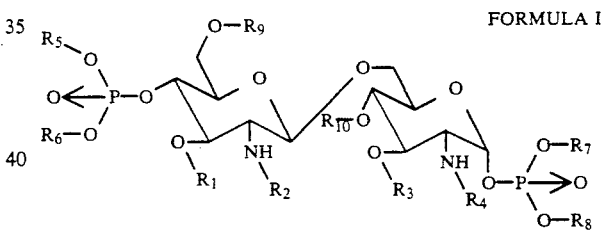

in which $R_1$, $R_2$, $R_3$ and $R_4$ are selected from hydrogen,

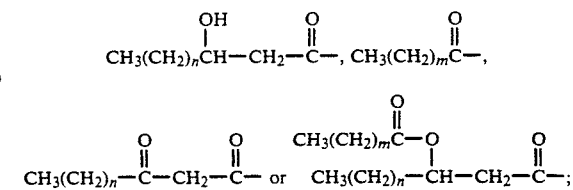

alkyl branched or 2-hydroxy fatty acyl group, wherein n is 1 to 14 and m is 2 to 16. The above groups can occur in various combinations.

The substituents on the phosphates ($R_5$, $R_6$, $R_7$, and $R_8$) can be H, lower alkyls of $C_1$ to $C_6$, an aryl, such as phenyl, naphthyl or the like. In addition, the phosphate group at the 4'-position can be cyclized with the hydroxyl group of the 6'-position ($R_9$).

The substitution at the 4- and 6'-positions ($R_{10}$ and $R_9$) can be a $C_1$ to $C_{16}$ alkyl group in an ether linkage, a $C_2$ to $C_{18}$ fatty acyl group in an ester linkage, or a straight or branched glycosidic residue from 1-20 glycosidic units per residue (preferably at $R_9$).

The glycosidic units can be glycopyranosyl or glycofuranosyl, as well as their amino sugar derivatives. The residues may be homopolymers, random, or alternating or block copolymers thereof. The glycosidic units have free hydroxy groups, or acylated hydroxy groups.

The glycosides can comprise up to 20 glycosidic units. Preferred, however, are those having less than 10, most preferred, those having 3 or less than 3 glycosidic units. Specific examples are those containing 1 or 10 glycosidic units in the glycoside residue.

Among the possible glycopyranosyl structures are glucose, mannose, galactose, gulose, allose, altrose, idose, or talose. Among the furanosyl structures, the preferred ones are those derived from fructose, arabinose or xylose. Among preferred diglycosides are sucrose, cellobiose, maltose, lactose, trehalose, gentiobiose, and melibiose. Among the triglycosides, the preferred ones may be raffinose or gentianose. Among the amino derivatives are N-acetyl-D-galactosamine, N-acetyl-D-glucosamine, N-acetyl-D-mannosamine, N-acetylneuraminic acid, D-glucosamine, lyxosylamine, D-galactosamine, and the like.

The glycosidic derivatives of the compounds of the present invention as well as the other lipid A derivatives can be prepared by standard synthetic methods well known to those skilled in the art.

In place of the compounds of Formula I, the compositions may contain purified nontoxic LPS from a species of Rhodopsuedomonas, such as R. sphaeroides and R. capsulata. The monophosphoryl lipid A (MPLA) and DPLA also are useful with the DPLA being preferred because of the larger molecular size. In the MPLA, the phosphate group can be either at the 1- or the 4′-position. The diacyl, triacyl, tetraacyl, pentaacyl, hexaacyl, and heptaacyl DPLA are all expected to be useful with the pentaacyl DPLA being preferred.

Especially preferred are the pentaacyl DPLAs obtained from the LPS of R. sphaeroides 55304 and R. capsulata 55303 grown at 26° C. They are the following:

1. 0-[2-amino-2-deoxy-$N^2$-(3-ketotetradecanoyl),$O^3$-(3-hydroxydecanoyl)-$\beta$-D-glucopyranosyl]-(1,6)-2-amino-2-deoxy-$N^2$-($\Delta^7$-tetradecanoyl-3-oxytetradecanoyl),$O^3$-(3-hydroxydecanoyl)-$\zeta$-D-glucopyranose 1,4′-bisphosphate.

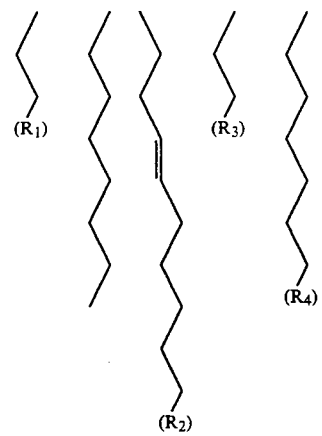

2. 0-[2-amino-2-deoxy-$N^2$-(3-ketotetradecanoyl),$O^3$-(3-hydroxydecanoyl)-$\beta$-D-glucopyranosyl]-(1→6)-2-amino-2-deoxy-$N^2$-(3-ketotetradecanoyl),$O^3$-($\Delta^9$-dodecenoyl-3-oxydecanoyl)-$\zeta$-D-glucopyranose 1,4′-bisphosphate.

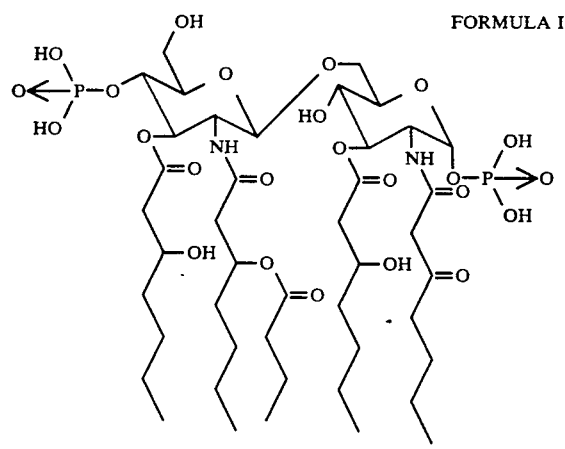

FORMULA II

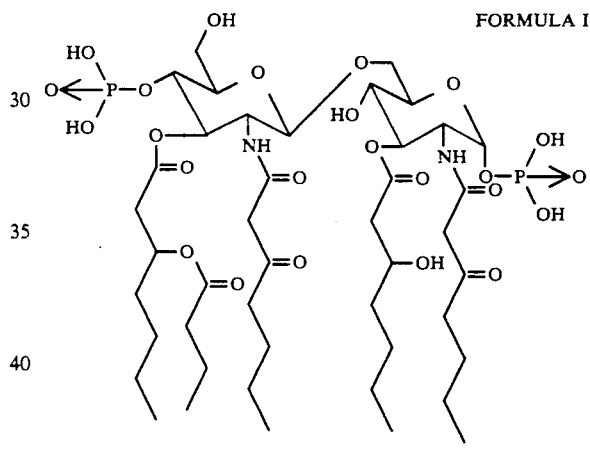

FORMULA III

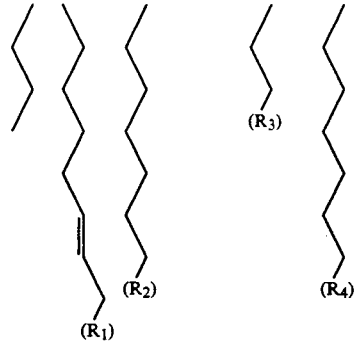

Other compounds represented by Formula I include the following

1. Monophosphoryl lipid A (MPLA).
2. Reduced DPLA.
3. Lipid X analog.
4. Tetraacyl, hexaacyl, and heptaacyl derivatives of lipid A. This includes the analog of precursor IVA. All of the above compounds may contain the 3-keto fatty acyl group at either/both 2- and 2′-position(s) of the sugar, a 3-hydroxy fatty acyl groups equal to or less than $c_{12}$ at the 3 and 3' in positions and possibly a double bond in the fatty acyl group at the 2'- and/or 3'-position.

Methods of Preparation

1. The MPLA can be prepared from the LPS by hydrolysis in 0.1N HCl at 100° C. for 30–60 min, followed by purification on either silicic acid or DEAE cellulose column.

2 A single fatty acid can be removed from a heptaacyl, hexaacyl or pentaacyl lipid A by hydrolysis in 0.033% (v/v) triethylamine at 100° C. to yield the corresponding hexaacyl, pentaacyl, and tetraacyl products, respectively.

3. All ester-linked fatty acids can be removed by deacylation reaction in 0.1M NaOH to yield the diacyl lipid A. Since the 3-ketotetradecanoate groups is N-linked, they will survive this hydrolysis.

4. Other unusual disaccharide lipid A's listed can be synthesized by the methods disclosed by Shiba et al.[34] The introduction of a keto fatty acid may pose a special synthetic problem.

5. The lipid X analogs can be synthesized by well established procedures. The introduction of a keto fatty acid may pose a special synthetic problem.

DESCRIPTION OF PREFERRED EMBODIMENT

In the preferred practice of the method of the invention the composition to be administered contains the DPLA prepared from the LPS of R. sphaeroides, having the identifying characteristics of the strain ATCC 55304, which has been grown at about 26° C.

The preferred DPLA is obtained by growing the R. sphaeroides photoheterotrophically in medium 550 (ATCC) at 26° C. (12–14 days) as previously described[14] and harvesting it by using a cell concentrator and centrifugation. For the extraction of the contaminating and unwanted pigments, 700 g of cell paste are extracted with stirring overnight at 22° C. with 4 liters of ethanol/n butanol (3:1). This extraction is repeated twice, then extracted once with 4 liters each of absolute ethanol, acetone and diethyl ether. The dry weight of the extracted light brown cells is 70.4 g. The LPS is extracted from 70.4 g of such a preparation to yield 640 mg (0.9%). This LPS preparation is suspended in 0.1M EDTA, pH 7.0 (at 1.0 mg/ml) and sonicated for 10 minutes as described by Qureshi et al.[15]. This suspension is stirred at 22° C. for 3 hours. The disaggregated LPS is recovered by extraction with chloroform/methanol to yield 310 mg of LPS.

The LPS is finally purified by the use of the reverse-phase SepPak cartridge (Waters Associates, Inc., Milford, Mass.). The cartridge is first washed with 10 ml of methanol. The LPS (30 mg) is loaded on a cartridge in 250 μl of chloroform/methanol (4:1) and washed successively with 10 ml of methanol, 20 ml of acetonitrile, and 20 ml of chloroform/methanol (4:1). The purified LPS is obtained from the last wash (25.7 mg, 86%).

The crude LPS (900 mg) is hydrolyzed in 0.02M sodium acetate, pH 2.5 at 2 mg/ml and incubated at 100° C. for 70 minutes to yield a mixture of monophosphoryl lipid A and several forms of DPLA's. The resulting DPLA product may be recovered by extracting with chloroform/methanol as previously described.[14] The DPLA can be purified by preparative thin layer chromatography on silica gel H (500 μm) at a load of 4 mg/20×20 cm plate using the solvent system of chloroform/methanol/water concentrated ammonium hydroxide (50:25:4:2). The DPLA band is visualized with iodine vapor and recovered from the silica gel by extraction with chloroform/methanol/water (66:33:4).

The mixture of monophosphoryl lipid A and the several forms of DPLA's can also be fractionated on a DEAE-cellulose column to yield the desired pentaacyl DPLA in highly purified form. The mixture (140 mg) is applied to a 3.5×29 cm column in the acetate form and the column is washed with 250 ml of chloroform/methanol/water (2:3:1). A linear gradient of 0.03 to 0.08M ammonium acetate in chloroform/methanol/water (2:3:1) is used to fractionate the DPLA. One hundred fifty fractions (13 ml) are collected and analyzed by spot charring to locate the DPLA. These fractions are analyzed by thin layer chromatography using silica gel H and the solvent system of chloroform/pyridine/formic acid/water (40:48:12:4). Specific fractions are pooled and desalted in a two-phase chloroform/methanol/water solvent. Peak A, fractions 14–19, contains the monophosphoryl lipid A (11.9 mg), Peak B fractions 52–61 (11.9 mg) containing an unidentified form of DPLA and Peak C, fractions 68–90 contains the purified pentaacyl/DPLA (42.9 mg). Alternatively, DPLA can be fractionated using a silicic acid column and the solvent system of chloroform/pyridine/formic acid/water. Peak B might also be useful in treating a mammal to protect it from the detrimental effects of the Gram negative endotoxin.

The DPLA thus obtained was unable to induce interleukin-1 release in murine peritoneal macrophage and blocked this activity by toxic deep rough chemotype LPS. These results along with the previously reported results on the tumor necrosis factor assay strongly suggests that the pentaacyl DPLA from R. sphaeroides lacks endotoxic activity and yet it is an effective antagonist of LPS-induced activation of macrophage.

A. PREPARATION OF LPS AND DPLA FROM R. SPHAEROIDES.

Example 1 and 2 describe a simple procedure for the preparation of highly purified pentaacyl DPLA from the LPS of R. sphaeroides. The DPLA was characterized by the combined reverse-phase HPLC and mass spectral analyses. It was found to antogonize the induction of IL-1 release by toxic Re LPS in murine macrophage. This indicated that the R. sphaeroides DPLA is not endotoxic.

EXAMPLE 1

Growth of Bacteria and Preparation of Lipopolysaccharide—R. sphaeroides ATCC 55304 was grown photoheterotrophically in medium 550 as previously described[14]. Cells were grown at 26° C. (12–14 days) and harvested by using a cell concentrator and by centrifugation. The cell paste (700 g) was extracted with stirring overnight at 22° C. with 4-1 of ethanol/n-butanol (3:1 v/v). This was repeated several times until all the pigments were removed. This was followed by extraction once with 4-1 of ethanol, twice with 3-1 of acetone and once with 4-1 of diethyl ether. LPS was extracted from 70.4 g of pigment-depleted cells using the method as described by Qureshi et al.,[34] yielding 640 mg of the LPS.

EXAMPLE 2

Preparation of the DPLA—The LPS (640 mg) obtained from R. sphaeroides was suspended in 0.02M sodium acetate, pH 2.5 at 3mg/ml incubated for 70 min at 100° C. and centrifuged at 8,000×g for 10 min. The pellet was dissolved in 60 ml of chloroform/methanol (2:1, v/v); 24 ml of water were added and then mixed. After standing the lower layer was recovered as previously described[15] to yield 240 mg of crude DPLA.

The crude DPLA (140 mg) was dissolved in 20 ml of chloroform/methanol (2:1, v/v) applied to a 3.5×29 cm DEAE-cellulose column (in acetate form), and the column was washed with 250 ml of chloroform/methanol/water (2:3:1, v/v). DPLA was eluted from the column using a linear gradient of 0.03–0.08M ammonium acetate in chloroform/methanol/water (2:3:1, v/v). One hundred and fifty 13 ml fractions were collected and analyzed for total phosphorous and the appearance of char-positive spots on a silica gel thin layer plate. Fractions giving char positive spots were analyzed by TLC using silica gel H plate and a solvent system of chloroform/pyridine/formic acid/water (10:12:3:1, v/v). Fractions containing the single TLC component were pooled and desalted in a two phase chloroform/methanol/water system as described previously[15]. The following pooled fractions were obtained. Peak A (14–19, 11.9 mg) containing the monophosphoryl lipid A (Rf=0.75 in the chloroform/pyridine/formic acid/water system mentioned above), Peak B (52–61, 11.9 mg) containing an unidentified form of DPLA (Rf =0.20) and peak C (67–87, 28.2 mg) containing the desired DPLA (Rf=0.59). Peak C represented the nontoxic highly purified pentaacyl DPLA.

For structural analysis the pentaacyl DPLA was converted to the free acid by passage through a Chelex 100 (Na+) and Dowex 50 (H+) double layer column in chloroform/methanol (4:1, v/v), methylated with diazomethane as described previously[35] and fractionated by HPLC.

HPLC fractionation—A 8 mm×10 cm Nova-Pak cartridge ($C_{18}$-bonded, end-capped 5μ silica, Waters Associates, Inc.) was used at a flow rate of 2 ml/min. For the fractionation of the *R. sphaeroides* tetramethyl DPLA, a linear gradient of 20–80% isopropanol in acetonitrile was used over a period of 60 min.

Mass Spectrometry—Plasma desorption mass spectra were obtained on a BIO-ION Nordic (Uppsala, Sweden), BIN-10K plasma desorption time-of-flight mass spectrometer equipped with a PDP 11/73-based data system. Purified DPLA was dissolved in chloroform/methanol (4:1, v/v) solution and electrosprayed onto a mylar backed aluminium foil. Positive ion mass spectra were recorded with an accelerating potential of 16 KV for 3 to 9 million primary events with resolution of 1 n sec/channel. H+ and Na+ were used for calebration.

FAB (fast atom bombardment) mass spectra were obtained on a Kratos (Manchester, England) MS-50 high resolution, double focussing mass spectrometer equipped with an Ion Tech (Teddington, England) saddle field atom gun. Samples were desorbed from the monothioglycerol matrix by a beam of 8 Kev Xe atoms. Positive ion spectra were recorded with an accelerating potential at 8 KV over the mass range of 2200-350 at a rate of 30 se/decade.

1L-1 assay—Peritoneal exudate cells were harvested from $BDF_1$ mice 48 h after an intraperitoneal injection of thioglycollate. Elicited macrophages were obtained as previously described[36]. Macrophages were either pretreated with *R. sphaeroides* DPLA (0.1–10 μg/ml) followed by the addition of toxic Re LPS (0.1 μg) after 2 h, or immediately stimulated with Re LPS (0.01–1.00 μg/ml). Control wells were treated with 10 μl of media containing 0.5% triethylamine. Cultures were incubated at 37° C. in the presence of 5% $CO_2$ for 18 h at which time the supernatants were collected and frozen at −20° C. until assayed. 1L-1 activity was determined by the comitogenic thymocyte assay.[25]

EXAMPLE 3

Effects of Pentaacyl DPLA on the Induction of 1L-1 in Murine Macrophages—Pentaacyl DPLA from *R. sphaeroides* tested at 0.1, 1.0, and 10 μg/ml was unable to induce 1L-1 in murine peritoneal macrophages. This compares with the toxic Re LPS which gave maximum induction at 0.1 μg/ml. In the blocking experiment 0.1, 1.0, or 10.0 μg/ml of pentaacyl DPLA was added to the cells 2 h prior to adding 0.1 μg/ml of the Re LPS. The addition of 1.0 μg/ml of pentaacyl DPLA (DPLA to Re LPS mass ratio of 10:1) caused a 60% inhibition of induction of 1L-1 release. When this ratio was increased to 100:1, the inhibition was total.

The pentaacyl DPLA from the LPS of *R. sphaeroides* is the first lipid A structure found to show no endotoxic activity and yet to be an effective antagonist of LPS induced activation of macrophages and B cells. This DPLA appears to compete favorably with toxic LPS for the active LPS/lipid A binding sites. For this reason, it can be a useful reagent to study the receptor-LPS interaction.

B. PREPARATION OF LPS, MPLA AND DPLA FROM *R. CAPSULATA*.

*R. capsulata* H. Gest strain St Louis (ATCC 55303) is grown photoheterotrophically in medium 550 at 26° C. for 12 days and harvested by using the cell concentrator and centrifugation. The cell paste (598 g) is extracted successively with stirring at 22° C. with 4 l of ethanol/butanol (3:1) for 2 h, the same solvent overnight, and acetone twice for 2h. The crude cell wall is prepared by suspending 50 g of the acetone-dried cells in 100 ml of 0.01M potassium phosphate buffer, pH 7.0. A French pressure cell is used to rupture the cells. The cells are centrifuged at 10,000×g for 30 min and the pellet is resuspended in 100 ml of the buffer by homogenizing. The suspension is centrifuged at 10,000×g and the pellet is recovered. This procedure is repeated twice and the pellet is finally washed with water and lyophilized to yield 14.5 g of crude cell wall.

The LPS is extracted from the cell wall preparation using a modified procedure of the hot phenol—water extraction[28]. The cell wall preparation (14.5 g) is suspended in 160 ml of water, sonicated for 10 min and heated to 68° C. Phenol (160 ml) is added to the suspension and stirred at 68° C. for 30 min. Then it is cooled to 4° C. and centrifuged at 10,000×g for 30 min. The phenol layer (lower layer) is recovered. This procedure is repeated twice with the cell wall pellet. All three phenol extracts are pooled and dialyzed against running tap water for 2 days. The impurities that precipitate out are filtered out with cheese cloth. The supernatant is again dialyzed against running water and finally with distilled water for 3 days. The dialyzed phenol layer which contains the LPS is lyophilized to yield 610 mg. The preparation of the MPLA and DPLA from the LPS of *R. capsulata* is identical to that described from the LPS of *R. sphaeroides*.

C. COMPARATIVE TESTS

To demonstrate the biological activity of the DPLA comparative studies were run in which the DPLA prepared from the LPS of *R. sphaeroides* was chosen to be the antagonist, because it is easily obtained in a highly purified form and it is similar to the toxic DPLA from the LPS of Salmonella typhimurium[25]. It was characterized as the tetramethyl derivative by plasma desorption mass spectrometry. It is nontoxic based on the chick embryo lethality test ($CELD_{50} > 20$ μg), and its structure is shown in Formula II.

For the antagonist to activate the RAW 264.7 murine macrophage cell line, we chose the toxic deep rough chemotype LPS (ReLPS) from Escherichia coli D31m4, which was recently purified and characterized[15]. We found that the DPLA from R. sphaeroides blocks the induction of cachectin (tumor necrosis factor, TNF) by the RAW 264.7 cells. This is a clear example of a lipid A derivative showing strong antagonism against a toxic agonist in the induction of cachectin.

The immunoblot method was used to quantitate the cachectin/TNF production by RAW 264.7 murine macrophage cells. RAW 264.7 cells[4,16] were seeded in 24-well plates (Nunc) at a density of $3 \times 10^5$ cells/well in Dulbecco's modified Eagle's medium supplemented with 5 percent fetal calf serum. After 12 hours, cell monolayers were washed twice with 1 ml of serum-free medium and then left covered with 2 μl of the same. An aqueous suspension of DPLA and/or ReLPS was then added to a final concentration indicated. Cells were incubated for 12 hours, after which the medium was removed for measurement of TNF by immunoblotting. One hundred μl of medium was mixed with 100 μl of SDS-containing sample buffer, heated to 100° C. for 5 minutes, and subjected to electrophoresis in a 10–15% polyacrylamide gradient gel. Proteins were then transferred to nitrocellulose electrophoretically, and TNF was visualized through the use of a rabbit anti-mouse TNF polyclonal serum[3,5] applied at a 1:100 dilution, followed by alkaline phosphatase-conjugated goat anti-rabbit IgG (Bio-Rad).

An immunoblot of cachectin/TNF produced by RAW 264.7 murine macrophage cells, showed induction by toxic ReLPS, lack of induction by DPLA (R. sphaeroides), and blocking of induction by the DPLA. Bands were visualized using nitroblue tetrazolium. Approximately 0.1 ng of cachectin/TNF may be detected as a band. The antiserum also recognized the processing intermediates (prohormones) on Western blot.

The immunoblot showed that the toxic ReLPS from E. coli caused the induction of cachectin by RAW 264.7 cells at all concentrations tested (1–100 ng/ml). Optimal induction occurred at 10 ng/ml of ReLPS. The DPLA of R. sphaeroides was not able to induce the formation of cachectin at 1–1000 ng/ml. We observed only slight induction at $10^4$ ng/ml. When DPLA of R. sphaeroides was added together with 10 ng/ml of ReLPS, we observed definite inhibition in the induction at $10^3$ ng/ml of DPLA (ReLPS to DPLA mass ratio of 1:100). This inhibition was probably maximal at $<10^4$ ng/ml (ratio of $1:<10^3$). Other lipid A analogs and precursors related to the toxic LPS, including monophosphoryl lipid A[23,25], lipid X[24], and precursor IVA[20] caused the induction of cachectin in RAW cells when analyzed by the immunoblot method and were not appropriate to use as inhibitors.

Pretreatment of mice (60 minutes and 90 minutes) with RsDPLA (100 μg and 1 mg) followed by E. coli LPS (1 μg and 5 μg) intraperitoneally showed that the DPLA blocked a rise in serum TNF. Similar results were seen with Guinea pigs (30 minutes and 1 mg RsDPLA and 10 μg LPS).

When the DPLA was analyzed for TNF production by RAW 264.7 cells using the indicator cell line L929, it also showed that the DPLA is not effective in the induction of TNF.

Table 1 shows that there is induction of TNF (cachectin) by ReLPS, lack of induction by DPLA and blocking of induction by pretreatment with DPLA using RAW 264.7 cells and indicator cell line L929.

TABLE 1

| | | | | |
|---|---|---|---|---|
| ReLPS (ng/ml) | 0.1 | 1.0 | 10 | 100 |
| Dilution to get 50% killing | 64 | 1440 | 1522 | 2344 |
| DPLA 10,000 (ng/ml) | | 10 | 100 | 1000 |
| Dilution to get 50% killing | 0 | 0 | 71 | 346 |
| DPLA 10,000 (ng/ml) | | 10 | 100 | 1000 |
| ReLPS (ng/ml) | 1.0 | 1.0 | 1.0 | 1.0 |
| Dilution to get 50% killing | 829 | 112 | 86 | 234 |
| % inhibition | 43 | 92 | 94 | 84 |

The RAW 264.2 macrophage tumor cell line was used. The TNF unit is derived by determining how far one can dilute the supernatant of the culture to achieve 50% killing of an indicator cell line.

The DPLA was added to the culture of RAW 264.2 2 hours before exposure to the ReLPS.

Interleukin-1 (IL-1) is another important mediator of lethality in Gram-negative sepsis. Competitive experiments similar to TNF assay were carried out in the induction of IL-1 using peritoneal macrophage. Peritoneal exudate cells were harvested from $BDF_1$ mice 48 h after an intraperitoneal injection of thioglycollate as described previously (Lederer and Czuprynki). Macrophages were either pretreated with R. sphaeroides DPLA (0.1–10 μg/ml) followed by addition of toxic ReLPS (0.1 μg), or immediately stimulated with ReLPS (0.01–1.00 μg/ml). Control wells were treated with 10 μl of media with 0.5% triethylamine. Cultures were incubated at 37° C. in the presence of 5% $CO_2$ for 18 h at which time the supernatants were collected and frozen at −20° C. until assayed. IL-1 activity was determined by the previously described comitogenic thymocyte assay (Meltzer, 1981).

Purified DPLA from R. sphaeroides had no IL-1/releasing activity (see Table 2). However, it blocked the release of IL-1 in peritoneal macrophages by ReLPS from E. coli in a concentration dependent manner. The ReLPS to DPLA mass ratios of 1:10 and 1:100 (when 0.1 μg of ReLPS was used) gave 60 and 100% inhibitions, respectively. These results further support the notion that the inhibition is due to the competitive binding by R. sphaeroides DPLA for the active sites on the macrophages.

TABLE 2

Inhibition by R. sphaeroides DPLA of induction of IL-1 in thioglycollate-elicited peritoneal macrophages by toxic ReLPS

| E. coli ReLPS (μg/ml) | R. sphaeroides DPLA (μg/ml) | Measure of IL-1 induction | | |
|---|---|---|---|---|
| | | CPM | CPM - Blank | % Inhibition |
| 1.0 | — | 43,353 (6657) | 35,565 | — |
| 0.1 | — | 58,565 (2432) | 50,777 | — |
| 0.01 | — | 13,610 (5312) | 5,822 | — |
| — | 10.0 | 3,764 (785) | 0 | — |
| — | 1.0 | 2,911 (383) | 0 | — |

TABLE 2-continued

Inhibition by *R. sphaeroides* DPLA of induction of IL-1 in thioglycollate-elicited peritoneal macrophages by toxic ReLPS

| E. coli ReLPS (µg/ml) | R. sphaeroides DPLA (µg/ml) | Measure of IL-1 induction | | % Inhibition |
|---|---|---|---|---|
| | | CPM | CPM - Blank | |
| — | 0.1 | 3,511 (616) | 0 | — |
| 0.1 | 10.0 | 5,892 (886) | 0 | 100 |
| 0.1 | 1.0 | 28,276 (4860) | 20,491 | 60 |
| 0.1 | 0.1 | 51,999 (4860) | 44,211 | 13 |

ReLPS was added to the culture 2 h after adding the *R. sphaeroides* DPLA. The triethylamine-medium blank was 7,788 (238). Standard deviation in CPM are given in parentheses.

At the very high concentration of DPLA of $10^4$ ng/ml, we did observe a measurable but low level in the induction of TNF. This confirms that results obtained by the immunoblot method. In the competition experiment, when 100 ng/ml of DPLA was added 2 hours before adding 1.0 ng/ml of the toxic ReLPS to the macrophage culture, it gave a 95 percent inhibition in the induction of TNF by ReLPS (ReLPS to DPLA mass ratio of 1:100). Even when only 10 ng/ml of DPLA was used in a similar experiment, 55 percent inhibition was observed (ReLPS to DPLA ratio of 1:10). When this ratio was increased to 1:$10^4$, the inhibition was lowered to 81 percent. This could be due to the ability of DPLA alone to induce TNF production at very high concentrations.

TABLE 3

| Treatment (ng/ml) | Dilution for 50% killing | Inhibition % |
|---|---|---|
| ReLPS | | |
| 0.1 | 180 | — |
| 1 | 5057 | — |
| 10 | 6272 | — |
| 100 | 8978 | — |
| DPLA | | |
| 10 | <10 | — |
| 100 | 19 | — |
| 1000 | 201 | — |
| 10000 | 764 | — |
| ReLPS (1.0 ng/ml) + DPLA | | |
| 10 | 2287 | 55 |
| 100 | 269 | 95 |
| 1000 | 201 | 96 |
| 10000 | 973 | 81 |

TNF unit was derived by determining dilution of culture supernatant that kills 50 percent of the indicator cell line.

DPLA was added 2 hours before exposing culture to ReLPS. The ReLPS and DPLA were complexed with bovine serum albumin.[1]

The compound DPLA was also shown to be inactive in the activations of 70Z/3 cells by toxic LPS. Table 4 shows the effect of pretreatment of 70Z/3 cells with DPLA on their activation by ReLPS.

TABLE 4

| ReLPS (µg/ml) | 0.003 | 0.01 | 0.1 | 0.3 |
|---|---|---|---|---|
| Activation[1] (% fluorescence) | 20.5 | 41 | 69 | 71.5 |
| DPLA (µg/ml) | 0.1 | 0.3 | 1.0 | 3.0 |
| ReLPS (µg/ml) | 0.1 | 0.1 | 0.1 | 0.1 |
| Activation[1] (% fluorescence) | 52 | 45 | 26.5 | 14 |

TABLE 4-continued

| % inhibition | 25 | 35 | 62 | 80 |
|---|---|---|---|---|

[1]Corrected for background of 5% fluorescence.
[2]The DPLA stimulated 70Z/3 pre-B cells to the extent of from 2.5–6.0% fluorescence at concentrations of 1.0–10 mg/ml. In the competitive inhibition experiment, the cells were first exposed to DPLA for 2 hours before adding the ReLPS. In all experiments, the ReLPS and DPLA were complexed with bovine serum albumin.

Table 5 shows the effect of concentration of ReLPS and DPLA on the activation of 70Z/3 cells.

TABLE 5

| ReLPS (µg/ml) 10 | DPLA (µg/ml) | | |
|---|---|---|---|
| | 0 | 1.0 | 3.0 |
| | Activation (% fluorescence)[1] | | |
| 0 | 0 | 3.5 | 2.56 |
| 0.1 | 73 | 28.5 (61) | 13.5 (92) | 4.5 (94) |
| 0.3 | 74 | 48.5 (34) | 30 (59) | 11 (85) |
| 1.0 | 75 | 57.5 (22) | 55 (26) | 25 (66) |
| 10 | 76 | 75.5 (0.5) | 77 (0) | 69 (9) |

[1]The % inhibition is indicated in parentheses.

Table 6 shows the effect of the addition of DPLA prior to or after the addition of ReLPS on the inhibition of activation of 70Z/3 cells.

TABLE 6

| Time of addition of[1] DPLA (hour) | Activation (% fluorescence) | % inhibition |
|---|---|---|
| −2 | 11 | 85 |
| 0 | 10.5 | 86 |
| 2 | 20 | 73 |
| 4 | 24 | 67 |
| 6 | 24.5 | 66 |
| 8 | 9.5 | 60 |
| 16 | 44 | 40 |
| 20 | 54 | 26 |
| 24 | 55.5 | 24 |

In this experiment, 0.1 µg/ml of ReLPS and 3.0 µg/ml of DPLA were used.
[1]The time of pre/post treatment of 70Z/3 cells with DPLA relative to the time of addition of ReLPS are indicated.

These results clearly show that the DPLA is able to effectively antagonize the induction of TNF by toxic ReLPS in a dose-dependent manner in RAW 264.7 cells. We have also shown that DPLA is an effective antagonist in the LPS-induced activation of 70Z/3 pre-B cells. DPLA and the lipid A moiety of the toxic ReLPS are structurally very similar, which strongly suggests that they both compete from the same active binding sites on the macrophage. Thus DPLA which can be prepared rather easily in highly purified form, also is a useful reagent in studying the nature of the LPS/lipid A binding to macrophages and perhaps to other responding cells.

These results are consistent with previous biological studies done with other types of lipid A analogs and LPS derivatives. Lipid X and its analog 3-aza-lipid X have been found to inhibit the LPS-induced neutrophil priming[6]. It has been suggested that these analogs compete with LPS for cellular binding sites. The selective deacylation of the non-hydroxyl fatty acids from LPS has been shown to render the new product less toxic and effective in inhibiting the neutrophil-endothelial cell interaction induced by LPS[12]. The competitive interaction of LPS and the deacylated LPS for specific cell-surface or intra-cellular target has been implicated.

The possible kinetics of this inhibition is revealed in a study that shows that the continued presence of LPS is required for TNF production[8]. Removal of LPS at any time results in abrupt cessation of further TNF production. One might then expect abrupt cessation of further TNF production after adding sufficient amounts of DPLA.

The lipid A moiety of toxic LPS acting on the macrophage is believed to play a central role in mediating endotoxic reactions[7,11]. It has been suggested that cachectin (TNF) is the mediator of lethality in Gram-negative sepsis. This is supported by several recent studies that included the use of recombinant TNF to induce many of the deleterious effects of endotoxin[2,10,17,26] and polyclonal antibody in passive immunization against cachectin[5]. Thus, the formation of cachectin might be a suitable target for pharmacotherapeutic intervention, therefore, DPLA also can be a useful inhibitor in this regard. DPLA is more effective than lipid X in protecting mice against a lethal dose of endotoxin as reported in the literature[13].

It also appears, that the pretreatment of mammals, such as sheep or mice, with DPLA should make them immediately resistant to the lethal effects of injection of Gram-negative endotoxin. This apparent antagonism between DPLA and endotoxin should have useful applications in clinical situations and disease states that are caused by endotoxin, such as Gram negative sepsis following surgery in humans and animals, bovine or porcine mastitis, and other endotoxin-related veterinary diseases listed in Table VI.

The lethal dose of E. coli endotoxin was determined both for the intravenous and for the intraperitoneal challenge. The lethal dose that killed 100% of the mice ($LD_{100}$) was 250 µg intravenously and 500 µg intraperitoneally. (It is important to standardize each lot of endotoxin with each lot of mice.) To determine the approximate dose of lipid A derivative needed to protect against a lethal challenge of endotoxin, mice are pretreated with the lipid A derivative intraperitoneally 2 hours before challenge with 1500 µg of endotoxin, which is 3 times the $LD_{100}$ dose. Pretreatment of mice with the lipid A derivative appeared to prolong the time to death.

Although the diphospholipids from E. coli and Salmonella strains are highly toxic, DPLA having the structure of the diphosphoryllipid A from R. sphaeroides is not. The $LD_{50}$ of DPLA in galactosamine—sensitized mice was greater than 20 mg/kg.

In contrast to treatment with the lipid A derivative (DPLA), a single injection of E. coli derived lipopolysaccharide (10–20 µg/kg) caused serious pulmonary hypertension, and after 15–30 minutes, an animal treated with the E. coli lipopolysaccharide began to tremble, cough and lay down. The symptoms became more severe over the next few hours and were accompanied by fever. About half the animals died by 24 hours.

Purified DPLA obtained from the nontoxic LPS of R. sphaeroides ATCC 55304 grown at about 26° C. was shown to block the induction of cachectin (TNF) in RAW 264.7 macrophage cell line by toxic deep rough chemotype LPS (ReLPS) of E. coli in a concentration-dependent manner. The ReLPS to DPLA mass ratios of 1:10 and 1:100 (when 1.0 ng/ml of ReLPS was used) gave 55 and 95 percent inhibitions respectively, in the induction of cachectin. Since the structure of the DPLA from R. sphaeroides is so similar to that of the lipid A moiety of the toxic ReLPS from E. coli, this inhibition is probably due to competitive binding by DPLA for the active sites on the macrophage. DPLA also should be a useful reagent to study the nature of LPS/lipid A binding in macrophage and perhaps other responding cells.

Previous work on the lethal endotoxicity of Gram-negative LPS demonstrates that limited prevention of the complications of injection of this material could be achieved through the administration of glucocorticoids, prostaglandins, naloxone, pressors, fluid replacement therapy or anti-LPS antibodies. In addition, all existing therapies against LPS lethality are dependent upon their being given prior to or very shortly after the administration of the LPS challenge.

The administration of a non-toxic lipid A derivative, such as DPLA, may ameliorate pathological conditions created by many of the endotoxin-induced diseases listed in Table VII. Furthermore, protection by the lipid A derivative may be obtainable even after endotoxin had been administered. This is an extremely important therapeutic consideration, since the signs and symptoms of a disease are almost always manifest before therapy is initiated. Although the mechanism(s) of protection by which the lipid A derivative is effective against LPS challenge remain unknown, the data fit best with competition for a common target molecule, such as membrane receptor(s) on endothelial or vascular cells.

Because lipid A derivatives having a 3-ketotetradecanoate instead of a 3-hydroxytetradecanoate at the 2-position and a $\Delta^7$-tetradecanoate instead of a tetradecanoate in acyloxyacyl linkage at the 2'-position, five fatty acids instead of six, and 3-hydroxy decanoate at the 3-position, instead of 3-hydroxy tetradecanoate of the glucosamine disaccharide of the LPS of R. sphaeroides grown at about 6° C. are not by themself toxic to animals, they may be useful for treatment of other diseases which LPS is known to ameliorate, but cannot be employed because of its toxicity. Thus, it might be anticipated that the lipid A derivatives would protect animals from skatole toxicity, oxygen toxicity, and drugs that enhance the production of free radicals (e.g. bleomycin, nitrofurantoin, adriamycin, etc.). It is known that LPS stimulates the activity of various enzymes that protect animals against oxidant stresses, and it can be anticipated that the non-toxic lipid A derivatives will have these beneficial effects as well.

D. EVALUATION OF IMMUNOMODULATORY EFFECTS

Bacterial lipopolysaccharides (LPSs) or endotoxins possess antitumor and adjuvant activity, as well as providing protection against X-irradiation and various bacterial infections. However, these beneficial effects have not been exploited to their fullest extent mainly because most LPS, even at very low doses, is extremely toxic and pyrogenic for most animal species. Both the beneficial and the harmful effects of LPS appear to be elicited by the diphosphoryl lipid A (DPLA) portion of the molecule; however, removal of a single phosphate group from the reducing end of DPLA yields monophosphoryl lipid A (MPLA). MPLA although less active then DPLA elicits all of the beneficial effects produced by native LPS, and it is relatively nontoxic and nonpyrogenic, even at high doses. Recent studies have shown that treatment of mice with MPLA results in an increase in the magnitude of the antibody response to Type III pneumococcal polysaccharide (SSS-III), as well as the synthesis of significant amounts of IgG antibody, not usually made after immunization with SSS-III alone. (Baker P. J. et al, Infect. Immun. 56: 1076–1083 and 3064–3066; 1988). These adjuvant or immunomodulatory effects have been attributed to the ability of MPLA to negate the inhibitory effects of thymus-derived (T) suppressor cells without altering the expression of amplifier or helper T cell function.

The LPS of *Rhodopseudomonas sphaeroides* ATCC 55304 (Rs-LPS) is nontoxic, as well as nonpyrogenic, and has a lipid A moiety similar in structure to that found in toxic enterobacterial and Salmonella LPS. Because of similarities in structure, the DPLA of nontoxic Rs-LPS can be used as an antagonist to block, in a concentration-dependent and a competitive manner, the induction of cachectin or tumor necrosis factor and the release of IL-1 by the toxic deep-rough chemotype LPS (Re-LPS) of *Escherichia coli*, as well as to block LPS-inducted immunoglobulin synthesis by 70Z/3 pre-B cells. This suggests that the DPLA of nontoxic Rs-LPS can compete effectively with toxic LPS for attachment to the cellular binding sites involved in triggering many of the pharmacological and immunological effects elicited by LPS. Rs-LPS, in addition to processing the aforementioned antagonistic effects, also is similar to MPLA in its ability to abrogate the expression of suppressor T cell ($T_s$) activity.

MATERIALS AND METHODS

Mice—Female BALBcByJ mice (age, 8 to 10 weeks; Jackson Laboratory, Bar Harbor, Me.) were used in most of the experiments to be described. Female athymic nude (nu/nu) mice, as well as their corresponding thymus-bearing (nu/+) littermate controls (age, 7 to 8 weeks), were obtained from the Frederick Cancer Research Center (Frederick, Md.); although these mice have the same genetic background and have been maintained in a closed colony for many years, their pedigree is not known.

MPLA—MPLA (average molecular size 1,718) was obtained from Ribi ImmunoChem Research, Inc. (Hamilton, Mont.). It was isolated from the heptoseless Re mutant, Salmonella typhimurium G30/C21, as described previously. Lyophilized MPL was reconstituted to 1 mg/ml in distilled water containing 0.2% triethylamine. It was mixed thoroughly and sonicated briefly to obtain an opalescent solution which was stored at 4° C. until use; the stock solution was diluted in Medium 199 to contain the desired amount of MPL to be added to cell suspensions. Information on the toxic and immunological properties of MPL is given elsewhere.

Antigens and immunization procedure—The immunological properties of the preparation of Type III pneumococcal polysaccharide (SSS-III) used and the method by which it was prepared have been described. For immunization, mice were given a single intraperitoneal (i.p.) injection of an optimally immunogenic dose (0.5 μg) SSS-III in 0.5 ml of saline. The magnitude of the antibody response produced was determined 5 days after immunization.

*Rhodopseudomonas sphaeroides* ATCC 55304 was grown photoheterotrophically in Medium 550 (American Type Culture Collection, Washington, D.C.) at 27° C. as described previously 14. The cells were first extracted with ethanol and normal butanol to remove pigments; then, the LPS was extracted by the method of Galanos et al. with modification 15. The resulting LPS was treated with 0.1M EDTA, pH 7.0, as described previously 15 and purified by using the reverse-phase Sep-Pak cartridges (Waters Associates, Inc., Milford, Mass.) to yield the Rs-LPS. This purified Rs-LPS has the structure as deduced by previous studies[14] and plasma desorption mass spectrometry: threonine-(glucuronic acid)$_3$-(3-deoxy-D-manno-octulosonic acid)-DPLA-ethanolamine.

LPS derived from *Escherichia coli* 0113 was purchased from Ribi ImmunoChem Research, Inc., Hamilton, Mont.

Immunological methods—Numbers of antibody-producing plaque-forming cells (PFCs) specific for SSS-III detected in individual mice provided a measure of the antibody response produced at the peak, i.e., 5 days after immunization (i.p.) with SSS-III. PFCs making antibody of the immunoglobulin M (IgM) class (>90% of all PFC found were detected by a slide version of the technique of localized hemolysis-in-gel using indicator sheep erythrocytes (SRBC) coated with SSS-III by the CrCl$_3$ method. Polyethylene glycol 6,000 (average molecular weight 6,000 to 7,500; J. T. Baker Chemical Co., Phillipsburg, N.J.) was added to the reaction mixture (melted agarose) at a final concentration of 0.25% (wt/vol) to improve the quality of the plaques found. Corrections were made (by subtraction) for the small number of background SRBC-specific PFCs present, so that only values for PFC making antibody specific for SSS-III (SSS-III-specific PFC) were considered. The values obtained (SSS-III-specific PFC per spleen), which are log normally distributed are expressed as the geometric mean (antilog) of the $\log_{10}$ number of PFCs per spleen for groups of similarly treated mice. This provides a reasonably good measure of the magnitude of the total antibody response produced, since SSS-III-specific PFC are detected only in the spleens of immunized mice.

Student's t test was used to assess the significance of the differences observed. Differences were considered to be significant when probability (P) values of <0.05 were obtained.

Assessment of polyclonal activity of LPS—Cells secreting non-antigen-specific immunoglobulin of the IgM class were detected by a modification of the protein A plaque assay, in which indicator SRBC were coated with protein A (Pharmacia), in the presence of 66 μg of CrCl$_2$ per ml as the coupling agent. The affinity-purified rabbit anti-mouse IgM used for the detection of non-antigen-specific IgM-secreting PFCs was the same preparation used in previous studies. A dilution (1:200 in saline) known to reveal maximal numbers of IgM-secreting PFCs was added (50 μl) to the soft agarose reaction mixture before the addition of spleen cells. Results were expressed as $\log_{10}$ IgM-secreting PFCs per spleen±standard error of the mean (SEM) for groups of LPS treated or untreated (control) mice.

Effect of treatment with Rs-LPS on the antibody response to SSS-III—Groups of mice were given (i.p.) different amounts of Rs-LPS, 2 days after immunization (i.p.) with an optimally immunogenic dose (0.5 μg) of SSS-III; the magnitude of the antibody (PFC) response elicited was determined, 5 days after immunization and compared to that of immunized control mice, not given Rs-LPS. The results obtained (Table 7) show that treatment with a single injection of 0.5 μg–10 μg of Rs-LPS had no effect (P>0.05) on the magnitude of the SSS-III-specific PFC response; however, a significant increase (about 2-fold; P<0.05) was noted for mice given 20 μg of Rs-LPS. In another experiment (Table 8) mice were given (i.p.) a single injection of 20 μg of Rs-LPS on the day of, or on different days after, immunization (i.p.) with 0.5 μg of SSS-III; the magnitude of the PFC response produced was assessed, 5 days after immunization and compared to that of control immunized mice, not given Rs-LPS. Treatment with Rs-LPS had no effect on the magnitude of the SSS-III-specific PFC response when given either on the day of immunization (Day 0) or one day after immunization (Day +1) with SSS-III (Table 8; $p>0.05$ in both cases); however, a significant increase in the SSS-III-specific PFC response was observed when Rs-LPS was given, 2 days after immunization (Day +2; $P<0.05$), and a greater increase was noted when Rs-LPS was given, 3 days after immunization with SSS-III (Day +3; $P<0.001$). Although significant enhancement of the PFC response also was noted when mice were given 20 µg of Rs-LPS, 4 days after immunization with 0.5 µg of SSS-III, the degree of enhancement obtained was no greater than that for mice given the same amount of Rs-LPS, 3 days after immunization with SSS-III. The results of these experiments are representative of the fact that a significant increase in the magnitude of the antibody (PFC) response to SSS-III can be demonstrated routinely in mice given 20 µg of Rs-LPS, 3 days after immunization with SSS-III. The effect of giving larger amounts of Rs-LPS was not examined so that the remaining experiments to be described could be completed using the same lot of Rs-LPS.

Effect on Rs-LPS on the induction and expression of low-dose immunological paralysis—Previous studies showed that prior exposure (priming) to a single injection of a marginally immunogenic dose of SSS-III results in the development of an antigen-specific form of unresponsiveness termed low-dose immunological paralysis. Such unresponsiveness, which requires at least 3 days to be induced fully, persists for several weeks or months after priming and is known to be mediated by Ts. Since treatment with MPLA has been shown to abolish the inhibitory effects of Ts, mice were given a single injection (i.p.) of different amounts of Rs-LPS either at the time of priming or three days after priming to determine if treatment with Rs-LPS alters the induction or expression of low-dose paralysis, respectively.

The data of Table 9 show that priming with a single injection of 0.005 µg of SSS-III results in the development of significant unresponsiveness, three days later as expected (Group A vs Group B, $p<0.001$). Treatment with 0.1 µg-10 µg of Rs-LPS, at the time of priming, partially reduced the degree of unresponsiveness induced (Group B vs Group C, D, or E, $p<0.02$); however, the remaining antibody (PFC)k response was still well below that of unprimed, immunized controls (Group A vs Group C, D, or E, $p<0.001$). Thus, treatment with Rs-LPS appears to have only a slight effect—at best—on the induction of low-dose paralysis. The effects of treatment with 0.2 µg-10 µg of Rs-LPS on the expression of fully induced low-dose paralysis were much more impressive (Table 10). Here, treatment with increasing amounts of Rs-LPS, 3 days after priming and at the time primed mice were immunized with 0.5 µg of SSS-III, resulted in a corresponding decrease in unresponsiveness (Group B vs Group C, $p<0.05$; Group B vs Group D or E, $p<0.001$). Although unresponsiveness was substantially reduced, it was not eliminated, even in primed mice given 10 µg of Rs-LPS (Group A vs Group E, $p<0.001$). In view of these findings, it was decided to examine whether treatment with more than one injection of Rs-LPS might be more effective than a single large dose in abolishing the expression of low-dose paralysis. This indeed appeared to be the case (Table 11). Treatment with two injections (i.p.) of 0.01 µg or 0.1 µg of Rs-LPS, at the time of immunization (Day 0) and one day after immunization (Day +1) with 0.5 µg of SSS-III greatly reduced the degree of unresponsiveness expressed (Group B vs Group C or D, $p<0.02$). More important, treatment with two injections of only 1 µg of Rs-LPS completely abolished unresponsiveness; here, the resulting PFC response did not differ significantly from that of unprimed immunized controls (Group A vs Group E, $p>0.05$).

Polyclonal activation of B cell IgM synthesis by Rs-LPS—Groups of mice were given a single injection (i.p.) of different amounts of Rs-LPS or E. coli 0113 LPS. Numbers of non-antigen-specified IgM-secreting PFC/spleen were determined 3 days later and the results obtained were compared to the baseline values for IgM-secreting PFC/spleen in unimmunized mice, not given LPS.

The data of Table 12 show that E. coli 0113 LPS is a very potent activator of polyclonal IgM synthesis since treatment with 10 µg of this preparation of LPS caused a significant increase (about 3-fold; $p<0.001$) in numbers of IgM-secreting PFC/spleen; in this case, all plaques detected were rather large and well-defined. By contrast, treatment with 10 µg-50 µg of Rs-LPS resulted in no significant change ($p>0.05$) in numbers of IgM-secreting PFC detected. Although the administration of 100 µg of Rs-LPS caused a significant ($p<0.001$) increase in IgM-secreting PFC, it should be noted that all plaques detected, though increased in number, were faint and not as well-defined as those found after the administration of E. coli 0113 LPS; this suggests a lower rate of IgM synthesis by such PFC. These findings indicate that Rs-LPS—even at high doses—is a very weak activator of polyclonal IgM synthesis. In view of these findings it appears that the augmented SSS-III-specific PFC response noted in the preceding experiments, in which mice were given 10 µg or 20 µg of Rs-LPS, cannot be attributed simply to the polyclonal activation of IgM synthesis.

Requirement for T cells in order to obtain Rs-LPS induced enhancement of the antibody response to SSS-III—Athymic nude (nu/nu) mice, as well as their genetically similar thymus-bearing controls (nu/+ mice) were given a single injection (i.p.) of 20 µg of Rs-LPS, 3 days after immunization (i.p.) with 05 µg of SSS-III. The magnitude of the SSS-III-specific PFC response produced was determined 5 days after immunization with SSS-III and the results obtained were compared to those for immunized nu/nu and nu/+ mice, not given Rs-LPS.

Treatment with 20 µg of Rs-LPS caused a significant increase (about 4-fold; $p<0.001$) in the SSS-III-specific PFC response of thymus-bearing nu/+ mice; however, no enhancement ($p>0.05$) was noted for immunized athymic nu/nu mice given Rs-LPS. These results are similar to those obtained in previous studies in which nu/nu and nu/+ mice were given MPL, 2 days after immunization with SSS-III. Thus, the ability of both Rs-LPS and MPL to augment the antibody (PFC) response to SSS-III is T cell dependent.

The results of Table 13 indicate that, in the absence of treatment with Rs-LPS, nu/nu mice make a better antibody response to SSS-III than thymus-bearing nu/+ mice. This is not an unusual finding since it has been noted in other studies. It is a reflection of the fact that B cells involved in the antibody response to SSS-III respond more effectively in the absence of the inhibiting effects of suppressor T cells present in nu/+ mice.

Inactivation of Ts activity after in vitro treatment with MPL or Rs-LPS—A pooled spleen cell suspension was prepared from mice, 18 24 h after prior exposure (priming) to a single injection (i.p.) of 0.005 μg of SSS-III. The cell suspension was adjusted with Medium 199 to contain $10 \times 10^7$ nucleated cells/ml and dispensed in 2.5 ml portions among several tubes. To each tube was added a known amount (0.005 ng to 5 μg) of either MPL or Rs-LPS in a volume of 50 μl; the contents were held at 4° C. for 30–60 minutes after mixing. Then, groups of mice were given (i.v.) $20 \times 10^6$ cells, in a volume of 0.2 ml, at the time of immunization (i.p.) with 0.5 μg of SSS-III; the magnitude of the SSS-III-specific PFC response elicited was determined, 5 days after immunization and compared to that of (a) immunized mice not given primed spleen cells, and (b) immunized mice given primed spleen cells not treated in vitro with either MPLA or Rs-LPS.

The transfer of $20 \times 10^6$ primed spleen cells not treated with MPLA caused significant ($p<0.05$) suppression of the PFC response as expected (Table 14); such suppression has been shown to be antigen-specific and mediated by Lyt-2+ Ts, activated following exposure to SSS-III. Treatment with all amounts of MPLA tested, including as little as 5ng of MPLA, abrogated the ability of primed cells to transfer suppression. Similar results were obtained when primed spleen cells were treated in vitro with Rs-LPS before transfer (Table 15); here, treatment with as little as 5 pg of Rs-LPS eliminated the suppressive effects of primed spleen cells. These findings attest to the fact that treatment with extremely small amounts of MPLA or Rs-LPS is very effective in inactivating the inhibitory effects produced by transferred Ts.

It should be noted that in these experiments, cells treated with MPLA or Rs-LPS were not washed prior to transfer to remove residual MPLA or Rs-LPS. In view of the extremely small amounts of MPLA and Rs-LPS used, this was not believed to be necessary since the administration of 10–50 μg of MPLA or 20 μg of Rs-LPS at the time of immunization with 0.5 μg of SSS-III does not influence the magnitude of the SSS-III-specific PFS response produced (Table 8).

The above described work which was done by P. J. Baker shows that, except for the doses used, the effects of treatment with Rs-LPS on the antibody response to SSS-III are similar to those described previously in studies conducted by P. J. Baker with MPLA. Both are without effect when given at the time of immunization with an optimally immunogenic dose of SSS-III; however, they elicit significant enhancement when give 2–3 days after immunization (Tables 7 & 8). In both cases, such enhancement is T cell-dependent and not due to the polyclonal activation of IgM synthesis by B cells (Tables 12 & 13). Treatment with Rs-LPS (Tables 9–11) or MPLA abrogates the expression—but not the induction—of low-dose immunological paralysis, a form of antigen-specific unresponsiveness known to be mediated by $T_s$. Other studies have established that the magnitude of the antibody response to SSS-III is regulated in a negative and positive manner by the competitive interaction of $T_s$ and amplifier T cells (T ), respectively. Since treatment with MPLA eliminates Ts activity, without altering the expression of T and helper T cell ($T_H$) function—(5), it appears that the immunomodulatory effects elicited by Rs-LPS—like those of MPLA—are mainly the result of eliminating the inhibitory effects produced by $T_s$ which are activated after exposure to SSS-III; this permits the positive effects of T to be more fully expressed, thereby resulting in an increased (enhanced) antibody response to an optimally immunogenic dose of SSS-III or the abrogation of low-dose immunological paralysis.

It should be noted that the aforementioned immunomodulatory effects can be demonstrated routinely after the in vitro injection of one or more doses of 1 μg–20 μg of Rs-LPS; however, larger amounts (50 μg–100 μg) of MPLA are usually required to obtain comparable results under the same experimental conditions. Although the reasons for this are not known, differences in molecular size may be a contributing factor. In contrast to Rs-LPS, which is a complex macromolecule, MPLA is a small molecule with an average molecular size of 1,718. Consequently, one might expect MPLA to be cleared from the circulation within a relatively short period of time post injection, thereby requiring larger amounts to produce a measurable effect. Alternatively, differences between Rs-LPS and MPL in their specific activity may be related to subtle differences in their chemical composition and/or structure.

The ability to transfer antigen-specific suppression with Lyt-2+ lymphocytes derived from mice previously exposed to SSS-III provides unequivocal proof that such unresponsiveness is indeed mediated by $T_s$ which play an active role in regulating the magnitude of the antibody response to SSS-III. The fact that prior treatment in vitro with minute amounts of nontoxic MPLA (Table 14) or Rs-LPS (Table (15) abolishes the capacity of such cells to transfer suppression indicates that both MPL and Rs-LPS are extremely effective in abolishing $T_s$ activity. Although the mechanism(s) by which this occurs remains to be defined, it surely must involve more than just the binding of Rs-LPS or MPLA to the surface of $T_s$; other studies have shown that the binding and subsequent elution of antigen-primed spleen cells from plastic dishes coated with MPLA results in >1,000-fold enrichment—not a decrease—of $T_s$ activity. Since neither T nor $T_H$ activity is impaired by treatment with large amounts of MPLA, it appears that Rs-LPS and MPLA, after binding to $T_s$, either (a) decrease their metabolic activity or (b) alter their distribution in tissues after cell transfer so that they can no longer influence the magnitude of the antibody response to SSS-III. Here, we assume that the former possibility requires Rs-LPS or MPL to be internalized a process which may not occur in the reaction between $T_s$ and MPL attached to an insoluble matrix, e.g., plastic dishes.

There is compelling evidence to indicate that cachectin or tumor necrosis factor (TNF) is the principle mediator of the lethal effects of endotoxin during Gram-negative bacterial infections. In this context, the administration of recombinant TNF has been shown to mimic many of the toxic effects ascribed to endotoxin whereas the infusion of polyclonal antibody specific for TNF neutralizes or blocks the expression of such effects. Thus, TNF appears to be an ideal target for pharmacotherapeutic intervention during severe endotoxemia. It has been reported that the nontoxic diphosphoryl lipid A (DPLA) of Rs-LPS, not only fails to induce the synthesis and release of TNF by macrophages, but also competes successfully with toxic LPS to block the induction of TNF in a dose-dependent manner. This suggests that nontoxic DPLA, as well as Rs-LPS, might be useful in the treatment of endotoxic shock. MPLA would not be appropriate here because it induces the formation of TNF. Furthermore, the ability of Rs-LPS to augment the antibody response by abrogating the inhibitory effects of $T_s$ suggests that Rs-LPS might also be effective in enhancing host immunity, thereby, resulting in a significant reduction of the amount of endotoxin elaborated during Gram-negative infection.

TABLE 7

Effect of Administering Different Amount of Rs-LPS on the 5 Day PFC Response to 0.5 µg of SSS-III.

| Treatment[a] | | SSS-III-specific | |
|---|---|---|---|
| SSS-III (µg) | Rs-LPS (µg) | PFC/spleen[b] | P value[c] |
| 0.5 | — | 4.379 ± 0.053 (23,933) | — |
| 0.5 | 0.5 | 4.427 ± 0.082 (26,715) | >0.05 |
| 0.5 | 1 | 4.537 ± 0.075 (34,404) | >0.05 |
| 0.5 | 10 | 4.527 ± 0.049 (33,626) | >0.05 |
| 0.5 | 20 | 4.614 ± 0.045 | <0.05 |

[a]Mice were given different amounts of Rs-LPS (i.p.), 2 days after immunization (i.p.) with 0.5 µg of SSS-III.
[b]Log$_{10}$ SSS-III-specific PFC/spleen ± SEM for 8 BALB/cByJ mice, 5 days after immunization (i.p.) with 0.5 µg of SSS-III; geometric means (antilogs) are in parentheses.
[c]Probability (P) values relative to immunized control mice, not given Rs-LPS.

TABLE 8

Numbers of SSS-III-specific PFC/spleen Detected in Mice Given 20 µg of Rs-LPS on Different Days Relative to Immunization with 0.5 µg of SSS-III.

| Day Rs-LPS Given[a] | SSS-III-specific PFC/spleen[b] | P Value[c] |
|---|---|---|
| — | 4.233 ± 0.063 (17,116) | — |
| 0 | 4.249 ± 0.047 (17,746) | >0.05 |
| +1 | 4.328 ± 0.067 (21,304) | >0.05 |
| +2 | 4.446 ± 0.055 (27,942) | <0.05 |
| +3 | 4.608 ± 0.048 | <0.001 |

[a]Day relative to immunization (Day 0) on which 20 µg of Rs-LPS was given (i.p.).
[b]Log$_{10}$ SSS-III-specific PFC ± SEM for groups of 10 BALBcByJ mice, 5 days after immunization (i.p.) with 0.5 µg of SSS-III; geometric means (antilogs) are in parentheses.
[c]Probability (P) values relative to control mice, not given Rs-LPS.

TABLE 9

Effect of Treatment with Rs-LPS on the Induction of Low-Dose Immunological Paralysis to SSS-III.

| | Treatment[a] | | | |
|---|---|---|---|---|
| | SSS-III | | | |
| Exptl. Group | Priming (0.005 µg) | Immunization (0.5 µg) | Rs-LPS (µg) | SSS-III-specific PFC/spleen[b] |
| A | — | + | — | 4.090 ± 0.066 (12,292) |
| B | + | + | — | 3.141 ± 0.093 (1,384) |
| C | + | + | 0.1 | 3.526 ± 0.079 (3,356) |
| D | + | + | 1 | 3.531 ± 0.102 (3,393) |
| E | + | + | 10 | 3.503 ± 0.078 (3,186) |

[a]Mice were pretreated (primed) with a single injection (i.p.) of 0.005 µg of SSS-III, 3 days before immunization (i.p.) with 0.5 µg of SSS-III. Rs-LPS was given (i.p.) at the time of priming with 0.005 µg of SSS-III.
[b]Log$_{10}$ SSS-III-specific PFC/spleen ± SEM for groups of 8 BALB/cByJ mice, 5 days after immunization (i.p.) with 0.5 µg of SSS-III; geometric means (antilogs) are in parentheses.

TABLE 10

Effect of Treatment with a Single Injection of Rs-LPS on the Express of Low-Dose Immunological Paralysis to SSS-III.

| | Treatment[a] | | | |
|---|---|---|---|---|
| | SSS-III | | | |
| Exptl. Group | Priming (0.005 µg) | Immunization (0.5 µg) | Rs-LPS (µg) | SSS-III-specific PFC/spleen[b] |
| A | — | + | — | 4.346 ± 0.072 (22,159) |
| B | + | + | — | 3.563 ± 0.064 (3,654) |
| C | + | + | 0.1 | 3.817 ± 0.078 (6,566) |
| D | + | + | 1 | 4.057 ± 0.047 (11,416) |
| E | + | + | 10 | 4.008 ± 0.055 (10,191) |

[a]Mice were pretreated (primed) with a single injection (i.p.) of 0.005 µg of SSS-III, 3 days before immunization (i.p.) with 0.5 µg of SSS-III. Rs-LPS was given (i.p.) at the time of immunization with 0.5 µg of SSS-III.
[b]Log$_{10}$ SSS-III-specific PFC/spleen + SEM for groups of 7-8 BALB/cByJ mice, 5 days after immunization (i.p.) with 0.5 µg of SSS-III; geometric means (antilogs) are in parentheses.

TABLE 11

Effect of Treatment with Two Injections of Rs-LPS on the Express of Low-Dose Immunological Paralysis to 0.5 µg SSS-III.

| | Treatment[a] | | | |
|---|---|---|---|---|
| | SSS-III | | | |
| Exptl. Group | Priming (0.005 µg) | Immunization (0.5 µg) | Rs-LPS (µg) | SSS-III-specific PFC/spleen[b] |
| A | — | + | — | 4.082 ± 0.051 (12,089) |
| B | + | + | — | 3.148 ± 0.153 (1,406) |
| C | + | + | 0.01 | 3.648 ± 0.078 (4,450) |
| D | + | + | 0.1 | 3.839 ± 0.090 (6,906) |
| E | + | + | 1 | 4.279 ± 0.099 (19,014) |

[a]Mice were pretreated (primed) with a single injection (i.p.) of 0.005 µg of SSS-III, 3 days before immunization (i.p.) with 0.5 µg of SSS-III. Rs-LPS was given (i.p.) at the time of immunization (day 0), and one day after immunization (Day +1) with 0.5 µg of SSS-III.
[b]Log$_{10}$ SSS-III-specific PFC/spleen ± SEM for groups of 9 BALBcByJ mice, 5 days after immunization (i.p.) with 0.5 µg of SSS-III; geometric means (antilogs) are in parentheses.

TABLE 12

Numbers of PFC Secreting Non-Antigen-Specific IgM in the Spleens of Non-Immunized Mice Given LPS.

| LPS (µg/mouse) | IgM-secreting PFC/spleen[a] | P Value[b] |
|---|---|---|
| — | 5.112 ± 0.038 (129,394) | — |
| E. coli 0113 LPS, 10 | 5.471 ± 0.041 (295,674) | <0.001 |
| Rs-LPS, 10 | 5.063 ± 0.040 (115,603) | >0.05 |
| Rs-LPS, 20 | 5.186 ± 0.050 (153,483) | >0.05 |
| Rs-LPS, 50 | 5.244 ± 0.105 (175,363) | >0.05 |
| Rs-LPS, 100 | 5.489 ± 0.059 (306,919) | <0.001 |

[a]Log$_{10}$ IgM-secreting PFC/spleen ± SEM for groups of 10 BALBcByJ mice, 3 days after the administration (i.p.) of LPS; geometric means (antilogs) are in parentheses.
[b]Probability (P) values relative to control mice, not given LPS.

TABLE 13

Effect of Treatment with 20 μg of Rs-LPS on the Magnitude of the 5 Day PFC Response of nu/nu and nu/+ Mice to 0.5 μg of SSS-III.

| Mice | Treatment[a] SSS-III (0.5 μg) | Rs-LPS (20 μg) | SSS-III-specific PFC/spleen[b] |
|---|---|---|---|
| nu/+ | + | − | 3.247 ± 0.134 (1,767) |
| nu/+ | + | + | 3.883 ± 0.130 (7,636) |
| nu/nu | + | − | 3.721 ± 0.119 (5,265) |
| nu/nu | + | + | 3.649 ± 0.103 (4,453) |

[a]Mice were given (i.p.) 20 μg of Rs-LPS, 3 days after immunization (i.p.) with 0.5˙ μg of SSS-III.
[b]Log$_{10}$ SSS-III-specific PFC/spleen ± SEM for groups of 10 nu/nu or nu/+ mice, 5 days after immunization (i.p.) with 0.5 μg of SSS-III; geometric means (antilogs) are in parentheses.

TABLE 14

Effect of In vitro Treatment with MPLA on the Ability of Primed Spleen Cells to Transfer Suppression.

| Cells Transferred and Treatment[a] | | SSS-III-specific | P |
|---|---|---|---|
| No. Primed Cells | MPLA | PFC/Spleen[b] | Value[c] |
| — | — | 4.133 ± 0.066 (13,598) | — |
| 20 × 10$^6$ | — | 3.952 ± 0.035 (8,947) | <0.05 |
| 20 × 10$^6$ | 5 ng | 4.162 ± 0.075 (14,505) | >0.05 |
| 20 × 10$^6$ | 0.5 μg | 4.030 ± 0.080 (10,716) | >0.05 |
| 20 × 10$^6$ | 5 μg | 4.058 ± 0.086 | >0.05 |

[a]Primed spleen cells were obtained from mice, 18-24 h after the administration (i.p.) of 0.005 μg of SSS-III: they were treated in vitro with different amounts of MPLA prior to transfer. Cells were transferred (i.v.) at the time of immunization (i.p.) with 0.5 μg of SSS-III.
[b]Log$_{10}$ SSS-III-specific PFC/spleen ± SEM for groups of 8 mice, 5 days after immunization (i.p.) with 0.5 μg of SSS-III; geometric means (antilogs) are in parentheses.
[c]P values based on comparisons to immunized controls not given primed cells.

TABLE 15

Effect of In vitro Treatment with Rs-LPS on the Ability of Primed Spleen Cells to Transfer Suppression.

| Cells Transferred and Treatment[a] | | SSS-III-specific | P |
|---|---|---|---|
| No. Primed Cells | Rs-LPS | PFC/Spleen[b] | Value[c] |
| — | — | 4.532 ± 0.064 (34,068) n = 9 | — |
| 20 × 10$^6$ | — | 4.271 ± 0.064 (18,662) n = 10 | <0.01 |
| 20 × 10$^6$ | 5 pg | 4.689 ± 0.059 (48,862) n = 10 | p > 0.05 |
| 20 × 10$^6$ | 5 ng | 4.564 ± 0.041 (36,635) n = 10 | p > 0.05 |
| 20 × 10$^6$ | 5 μg | 4.388 ± 0.057 (24,453) n = 10 | p > 0.05 |

[a]Primed spleen cells were obtained from mice, 18-24 h after the administration (i.p.) of 0.005 μg of SSS-III; they were adjusted to contain 100 × 10$^6$ nucleated cells/ml. Different amounts of Rs-LPS, in a volume of 50 ul, were added to 2.5 ml of the resulting cell suspension; the mixture was held at 4° C. for about 30 minutes, after which 20 × 10$^6$ cells were transferred (i.v.) at the time of immunization (i.p.) with 0.5 μg of SSS-III.
[b]Log$_{10}$ SSS-III-specific PFC/spleen ± SEM for groups of n mice, 5 days after immunization (i.p.) with 0.5 μg of SSS-III; geometric means (antilogs) are in parentheses.
[c]P values based in comparisons to immunized controls, not given primed cells.

To summarize in the foregoing experiments, the antibody responses of mice immunized with Type III pneumococcal polysaccharide (SSS-III) were examined with and without treatment with nontoxic lipopolysaccharide from *Rhodopseudomonas spaeroides* (Rs-LPS). The results obtained were similar to those described previously for mice treated with monophosphoryl lipid A (MPLA) except that much lower concentrations of Rs-LPS were needed. Both were without effect when given at the time of immunization with SSS-III but elicited significant enhancement when given 2-3 days later. Such enhancement was T cell dependent and not due to polyclonal activation of IgM synthesis by B cells. Treatment with either Rs-LPS or MPL abolished the expression but not induction of low-dose paralysis, a form of immunological unresponsiveness known to be mediated by suppressor T cells ($T_s$). An in vitro treatment of cell suspensions containing $T_s$ with 5 pg of Rs-LPS or 5 ng of MPL per 2.0×10$^7$ cells completely eliminated the capacity of such cells to transfer suppression to other mice. These findings indicate that the immunomodulatory effects of both MPLA and Rs-LPS are mainly the result of eliminating the inhibitory effects of $T_s$; this permits the positive effects of amplifier T cells (T ) to be more fully expressed.

In an effort to determine which structural features contributed to the non-toxic nature of the preferred compounds comparative tests were run with reduced RsDPLA and reduced *E. coli* DPLA in the extremely sensitive assay of pruning of macrophage by LPS/lipid A for PMA-stimulated superoxide anion release. The reduced RsDPLA like the unreduced RsDPLA was inactive or non-toxic and the reduced *E. coli* DPLA was just as active or toxic as the unreduced. The conclusion is that the presence of the keto fatty acid and the unsaturated fatty acid does not play a structural role in non-toxicity. The important features must be (a) the presence of five fatty acids in the RsDPLA vs. six fatty acids in *E. coli* DPLA and (b) the presence of a OH at $C_{10}$ at the 3-position of RsDPLA vs. the OH at $C_{14}$ in the *E. coli* DPLA.

In the method of the present invention the lipid A derivatives are preferrably introduced into the circulation of an animal by intravenous, intraperitoneal or intramuscular routes, and appear to induce a state of relative resistance to the deleterious effect of LPS. When thus employed, the compounds may be administered in the form of parenteral solutions containing the selected protective compound in a sterile liquid suitable for intravenous or other administration. There also may be instances in which the non-toxic lipid A derivatives are best administered orally or topically. When intended for such indications the compounds may be combined with pharmaceutical deluents and the like and formed into dosage form suitable for oral application, such as capsules or tablets, or topical application, such as patches or ointments. The exact route, dose, and administration interval of the selected compound will vary with the size and weight of the animal, and the species, and the desired level of protection. Generally, the dosages will range from about 1 mg to about 100 mg per kilogram of body weight.

In one embodiment of the method of the present invention the compounds might be employed as adjuvants with vaccines to enhance the production of protective immunoglobulin. In another embodiment, the compounds might be combined with corticosteroids or anti TNF factors. The rationale for the use of DPLA with an anti TNF drug or agent is that the DPLA can block the LPS so that anti TNF agent can attack the TNF.

REFERENCES

1. Appelmelk, A. J., A. M. J. J. Verweij-Van Vught, D. M. MacLaren, and L. G. Thijs. 1985. An enzyme-linked immunosorbent assay (ELISA) for the measurement of antibodies to different parts of the Gram negative lipopolysaccharide core region. J. Immunol. Methods 82:199-207.
2. Bauss, F., W. Droge, and D. N. Mannel. 1987. Tumot necrosis factor mediates endotoxic effects in mice. Infect. Immun. 55:1622-1625.
3. Beutler, B., N. Krochin, I. W. Milsark, C. Luedke, and A. Cerami. 1986. Control of cachectin (tumor necrosis factor) synthesis: mechanism of endotoxin resistance. Science 222:977-980.
4. Beutler, B., J. Mahoney, N. LeTrang, P. Pekala, and A. Cerami. 1985. Purification of cachectin, a lipoprotein lipases-suppressing hormone secreted by endotoxin-induced RAW 264.7 cells. J. Exp. Med. 161:984-995.
5. Beutler, B., I. W. Milsark, and A. Cerami. 1985. Passive immunization against cachectin/tumor necrosis factor protects mice from lethal effect of endotoxin. Science 229:869-871.
6. Danner, R. L., K. A. Joiner, and J. E. Parrillo. 1987. Inhibition of endotoxin-induced priming of human neutrophils of lipid X and aza-lipid X. J. Clin. Invest. 80:605-612.
7. Freudenberg, M. A., D. Keppler, and C. Galanos. 1986. Requirement for lipopolysaccharide-responsive macrophages in galactosamine-induced sensitization to endotoxin. Infect. Immun. 51:891-895.
8. Gifford, G. E., and M. L. Lohmann-Matthes. 1986. Requirement for the continued presence of lipopolysacchatide for production of tumor nectosis factor by thioglycollate-induced peritoneal murine machrophages. Int. J. Cancer 38:135-137.
9. Imoto, M., S. Kusumoto, T. Shiba, E. Th. Rietschel, C. Galanos, and O. Luderitz. 1985. Chemical structure of Escherichia coli lipid A. Tetrahedron Lett. 26:907-908.
10. Lehman, V. M., M. A. Freudenberg, and C. Galanos. 1987. Lethal toxicity of lipopolysaccharide and tumor necrosis factor in normal and D-galactosamine-treated mice. J. Exp. Med. 165:657-663.
11. Morrison, D.C. 1983. Bacterial endotoxins and pathogenesis. Rev. Infect. Dis. 5:S733-S747.
12. Pohlman, T. H., R. S. Munford, and J. M. Harlan. 1987. Deacylated lipopolysaccharide inhibits neutrophil adherence to endothelium induced by lipopolysaccharide in vitro. J. Exp. Med. 165:1393-1402.
13. Proctor, R. A., J. A. Will, K. E. Burhop, and C. R. H. Raetz. 1986. Protection of mice against lethal endotoxemia by a lipid A precursor. Infect. Immun. 52:905-907.
14. Qureshi, N., J. P. Honovich, H. Hara, R. J. Cotter, and K. Takayama. 1988. Location of fatty acids in lipid A obtained from lipopolysaccharide of Rhodopseudomonas sphaeroides ATCC 17023. J. Biol. Chem. 263:5502-5504.
15. Qureshi, N., K. Takayama, P. Mascagni, J. Honovich, R. Wong, and R. J. Cotter. 1988. Complete structural determination of lipopolysaccharide obtained from deep rough mutant of Escherichia coli. Purification by high performance liquid chromatography and direct analysis by plasma desorption mass spectrometry. J. Biol. Chem. 263:11971-11976.
16. Raschke, W. C., S. Baird, P. Ralph, and I. Nakoinz. 1978. Functional macrophage cell lines transformed by Abelson leukemia virus. Cell 15:261-269.
17. Remick, D. G., J. Larrick, and S. L. Kunkel. 1986. Tumor necrosis factor-induced alterations in circulating leukocyte populations. Biochem. Biophys. Res. Commun. 141:818-824.
18. Salimath, P. V., R. N. Tharanathan, J. Weckesser, and H. Mayer. 1983. Structural studies on the non-toxic lipid A from Rhodopseudomonas sphaeroides ATCC 17023. Eur. J. Biochem. 136:195-200.
19. Salimath, P. V., R. N. Tharanathan, J. Weckesser, and H. Mayer. 1984. The structure of the polysaccharide moiety of Rhodopseudomonas sphaeroides ATCC 17023 lipopolysaccharide. Eur. J. Biochem. 144:227-232.
20. Strain, S. M., I. M. Armitage, L. Anderson, K. Takayama, N. Qureshi, and C. R. H. Raetz. 1985. Location of polar substituents and fatty acyl chains on lipid A precursors from a 3-deoxy-D-manno-octulosonic acid-deficient mutant of Salmonella typhimurium. Studies by 1H, 13C, and 31p nuclear magnetic resonance. J. Biol. Chem. 260:16089-16098.
21. Strittmatter, R., J. Weckesser, P. V. Salimath, and C. Galanos, 1983, Nontoxic lipopolysaccharide from Rhodopseudomonas sphaeroides ATCC 17023. J. Bacteriol, 155:153-158.
22. Takayama, K., and Qureshi, N. 1986. Structures of lipid A, its precursors, and derivatives, p. 5-8, In L. Leive (ed.), Microbiology-1986. American Society for Microbiology, Washington, D.C.
23. Takayama, K., N. Qureshi, and P. Mascagni. 1983. Complete structure of lipid A obtained from the lipopolysaccharides of the heptoseless mutant of Salmonella typhimurium. J. Biol. Chem. 258:12801-12803.
24. Takayama, K., N. Qureshi, P. Mascagni, M. A. Nashed, L. Anderson, and C. R. H. Raetz. 1983. Fatty acid derivatives of glucosamine-1-phosphate in Escherichia coli and their relation to lipid A. Complete structure of a diacyl GlcN-1-P found in a phosphatidylglycerol-deficient mutant. J. Biol. Chem. 258:7379-7385.
25. Takayama, K., N. Qureshi, E. Ribi, and J. L. Cantrell. 1984. Separation and characterization of toxic and nontoxic forms of lipid A. Rev. Infect. Dis. 6:439-443.
26. Tracy, K. J., B. Beutler, S. F. Lowry, J. Merryweather, E. Wolpe, I. W. Milsark, R. J. Haririr, T. J. Fahey Iii, A. Zentella, J. D. Albert, G. T. Shires, and A. Cerami. 1986. Shock and tissue injury induced by recominant human cachectin. Science 234:470-474.
27. Omar, A. S., Flammann, H. T., Borowiak, D. and Weckesser, J. 1983. Liposaccharides of two strains of the phototropic bacterium Rhodopsuedomonas Capsulata, Arch. Microbiol. 134:212-216.
28. Westphal, O., Liideritz, O., Bester, F. (1952) liberdie Extraktion von Bakterier mit Phenol/Wasser. Z. Naturforsch 7b:148-155.
29. Imoto, M., Yoshimura, H., Yamamoto, M., Shimamoto, T., Kusumoto, S., and Shiba, T. (1984) Chemical synthesis of phosphorylated tetra-acyl disaccharide corresponding to a biosynthetic precursor of lipid A. Tetrahedron Lett. 25, 2667-2670.
30. Imoto, M., Yoshimura, H., Sakaguchi, N., Kusumoto, S., and Shiba, T. (1985) Total synthesis of Escherichia coli lipid A. Tetrahedron Lett. 26, 1545-1548.

31. Kusumoto, S., Yamamoto, M., and Shiba, T. (1984). Chemical synthesis of lipid X and lipid Y, acyl glucosamine 1-phosphate isolated from *Escherichia coli* mutants. Tetrahedron Lett. 25, 3727–3730.

32. Lederer, J. A., and Czuprynki, C. J. Purification of bovine interleukin from LPS stimulated monocytes. Vet. Immunol. (in press).

33. Meltzer, M. S. 1981. Peritoneal mononuclear phagocytes from small animals in Methods for studying mononuclear phagocytes. Editor D. O. Adams, P. J. Edelson and H. Koren Academic Press New York 1981.

34. Qureshi, N., Mascagni, P., Ribi, E., and Takayama, K. (1985) J. Biol. Chem. 260, 5271–5278.

35. Lederer, J. A., Czuprynski Vet. Immunol. (in press).

36. Meltzer, M. S. (1981) Methods for studying mononuclear phagocytes (Adams, D. O., Edelson, P. J. and Koren, H. eds), Academic Press, New York 63–68.

We claim:

1. A method of stimulating the immune cells of an animal by negating the inhibitory effects of thymus-derived T suppressor cells without altering the expression of amplifier or helper T cell functions, which method comprises administering to said animal a safe and effective amount of a compound selected from the non-toxic lipopolysaccharide (LPS) of a species of Rhodopsuedomonas or a compound which has the following structural formula:

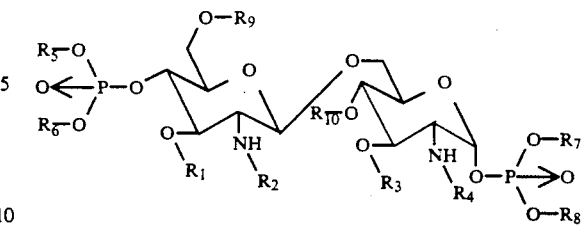

in which $R_1$, $R_2$, $R_3$ and $R_4$ are the same or different and are hydrogen,

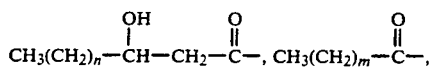

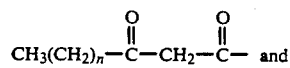

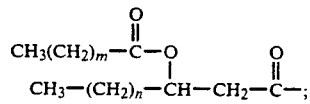

alkyl branched or 2-hydroxy fatty acyl group $R_5$, $R_6$, $R_7$ and $R_8$ are the same or different and selected from hydrogen, a lower alkyl of 1 to 6 carbon atoms, an aryl; and $R_9$ and $R_{10}$ are selected from a lower alkyl of 1 to 6 carbon atoms in an ether linkage, a $C_2$ to $C_{18}$ fatty acyl group in an ester linkage or a glycosidic residue from 1 to 20 glycoside units per residue or $R_9$ and $R_{10}$ are cyclized, and n is 1 to 14 and m is 2 to 16.

2. The method of claim 1 in which the compound is diphosphoryl lipid A (DPLA).

3. The method of claim 1 in which the monophosphoryl lipid A (MPLA).

4. The method of claim 1 in which the compound is lipopolysaccharide (LPS) selected from *Rhodopsuedomonas sphaeroides* and *Rhodopsuedomonas capsulata*.

5. A pharmaceutical dosage form containing an immunostimulating amount of a compound of claim 1.

6. The method of claim 1 in which the compound is employed as an adjuvant.

* * * * *